United States Patent [19]
Everett

[11] 4,086,057
[45] Apr. 25, 1978

[54] ULTRASONIC DISINFECTION SYSTEM

[76] Inventor: William Clinton Everett, 11745 Seventh Way, North (Apt. #7), St. Petersburg, Fla. 33702

[21] Appl. No.: 709,288

[22] Filed: Jul. 28, 1976

[51] Int. Cl.² .................. A61L 1/00; B05B 17/06; A23L 3/30
[52] U.S. Cl. .................. 21/54 A; 21/102 A; 21/DIG. 2; 204/157.1 S; 210/19; 239/4; 239/102; 99/451
[58] Field of Search .............. 21/102 R, 102 A, 54 R, 21/54 A, DIG. 2; 210/19; 426/238; 239/4, 102; 204/157.1 S; 259/DIG. 44; 99/451

[56] References Cited
U.S. PATENT DOCUMENTS

| | | | |
|---|---|---|---|
| 2,717,874 | 9/1955 | Verain | 210/19 |
| 3,072,808 | 1/1963 | Plesset et al. | 259/DIG. 44 |
| 3,537,655 | 11/1970 | Gustafson | 210/19 X |
| 3,672,823 | 6/1972 | Boucher | 21/54 A X |
| 3,772,188 | 11/1973 | Edwards | 210/19 X |
| 3,966,120 | 6/1976 | Furgalus et al. | 239/102 |
| 4,003,832 | 1/1977 | Henderson et al. | 21/102 A X |
| 4,013,552 | 3/1977 | Kreuter | 210/19 X |

FOREIGN PATENT DOCUMENTS

| | | | |
|---|---|---|---|
| 873,798 | 7/1961 | United Kingdom | 204/157.1 S |
| 1,100,535 | 1/1968 | United Kingdom | 239/102 |

Primary Examiner—Morris O. Wolk
Assistant Examiner—Roger F. Phillips
Attorney, Agent, or Firm—Maky, Renner, Otto & Boisselle

[57] ABSTRACT

In a system for the disinfection of liquids containing live bacteria, the liquid is directed through a nozzle onto an external surface of an ultrasonic transducer whereby said liquid is subjected to ultrasonic energy at a specific frequency and power for a predetermined period of time so as to achieve a desired and controlled degree of kill of said bacteria.

5 Claims, 4 Drawing Figures

U.S. Patent
April 25, 1978
4,086,057
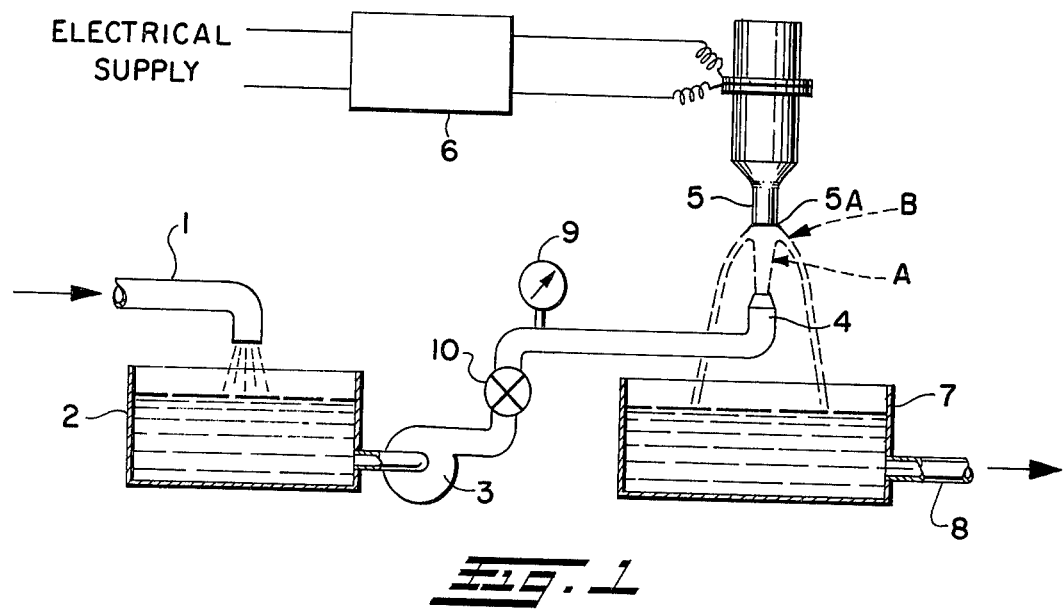
_Fig. 1_
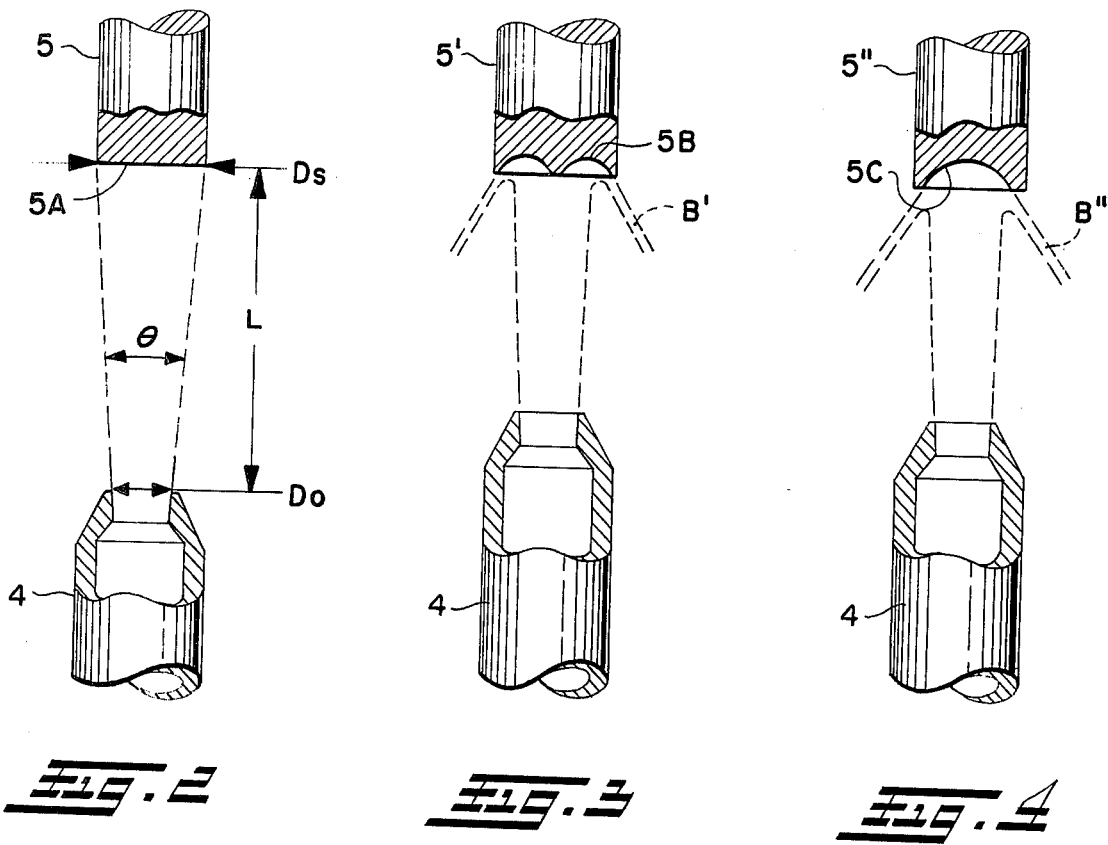
_Fig. 2_  _Fig. 3_  _Fig. 4_

ULTRASONIC DISINFECTION SYSTEM

BACKGROUND OF THE INVENTION

Ultrasonic energy can be defined for our purposes as the form of wave energy transmitted through liquids at sonic velocity and ultrasonic (i.e. above about 15 kHz) frequency. This type of energy has been used previously in conjunction with chemical solutions and/or ultra-violet light to disinfect liquids containing harmful or undesirable micro-organisms including bacteria. It is also known to use ultrasonic energy in conjunction with high liquid pressures (typically at 1000 lb./square inch pressure) for the same purpose. Disinfection is generally understood to mean destroying or killing the micro-organisms and it is believed that the destruction is due to the violent local changes in liquid velocity and pressure associated with the ultrasonic waves.

There are situations, however, such as are involved in treating sewage or drinking water, where it is not convenient or desirable to employ either chemical solutions, ultra-violet light or high liquid pressures in conjunction with ultrasonic energy. In such applications, the liquid has to be treated continuously while flowing and the problem arises of how this is to be done.

If the liquid is treated while flowing in a pipe or channel, then the ultrasonic energy may be dissipated (i.e. lost by absorption in the containing walls of the pipe or channel). It is known to employ an ultrasonic energy source in the form disclosed by U.S. Pat. No. 3,966,120 wherein the liquid to which the energy is supplied is forced through a nozzle(s) onto the active surface of an ultrasonic transducer in an open atmosphere; the liquid then flows from the active surface as a sheet which eventually breaks up into drops and is collected in a suitable receiving tank. The advantage of this particular method is that the ultrasonic energy is transmitted to the liquid with only negligible loss since the liquid jet is surrounded by air rather than the solid walls of a pipe or channel.

SUMMARY OF THE INVENTION

The present invention comprises a method and system for subjecting a liquid while flowing as a free jet stream to continuous exposure to a source of ultrasonic energy. The rate of flow of the liquid is controlled in relation to the energy source so as to obtain effective disinfection of liquid. In a preferred embodiment the liquid jet is directed against an ultrasonically vibrating surface to insure that all the liquid is exposed to the energy source for a sufficient length of time.

BRIEF DESCRIPTION OF THE DRAWING

FIG. 1 is a diagrammatic representation of a liquid disinfecting system according to the present invention; and FIGS. 2-4 illustrate various forms of ultrasonically vibrated surfaces against which a jet of liquid to be disinfected is directed.

DETAILED DESCRIPTION OF THE DRAWING

The general arrangement of the system employed is shown in FIG. 1 in diagrammatic representation. The liquid to be treated flows from its origin through a pipe 1 into a tank 2 from which it is pumped by a suitable pump 3 through a control valve 10 to an orifice 4 arranged to produce a jet A of the liquid which contacts and flows over the active surface 5A of an ultrasonic transducer 5 which is energized from a generator 6 supplied with electricity from a suitable source. The liquid leaves surface 5A in the form of an umbrella-shaped sheet B which breaks up eventually into drops and is collected in a tank 7 from which it is led through an outlet 8 to its intended use. It will be understood that this system may contain screens, filters, valves, switches etc. which are normally used in any liquid flowing system and are not an essential part of the invention. Furthermore the invention is not limited to a vertical arrangement of the liquid jet and transducer as shown here and any suitable method of collecting the treated liquid may be employed as long as the jet A is in free contact with the surrounding atmosphere.

The geometric relationship of the orifice 4 and surface 5A is shown in greater detail in FIG. 2 wherein the axis of the liquid jet is common with the axis of the ultrasonic transducer horn 5. If both the orifice and the surface are circular then $D_o$, the diameter of the orifice, must be less than $D_s$, the diameter of the surface; the distance L is adjusted so that the angle $\theta$ is approximately 5°. This relationship insures that the whole of the liquid issuing from the orifice 4 is exposed to the ultrasonic wave energy produced at the surface 5A. For example, if $D_s = 0.625$ inches and $D_o = 0.375$ inches then $L =$ approximately 3.0 inches. Expressed in general terms $L/(D_s - D_o) = 12$ approximately in consistent units. It will be understood however that the distance L may be reduced somewhat in order to produce a particular shape of liquid sheet B', as shown in FIG. 3. In this case the active surface of the horn 5' is formed as a circular groove 5B starting at a cusp in the center and extending to the outer edge of the horn 5'; by this means the liquid sheet is deflected symmetrically to form a narrow umbrella-shape, which may be made more suitable for some installations of the invention by making the width of the liquid jet near the surface 5B less than the diameter D, which is achieved by reducing the distance L. In FIG. 4, the active surface 5C of the horn 5" includes a central depression in the form of a spherical segment to alter the pattern of the liquid sheet B" as shown.

The rate of flow of the liquid through the orifice 4 can be controlled as is well known by varying either the orifice size or the liquid pressure-difference across the orifice. In a typical embodiment of the invention the liquid pressure-difference as indicated by a pressure gauge 9 in FIG. 1 can vary from 2.5 to 44 lb./square inch, and $D_o = 0.3125$ inches. The rate of flow of liquid therefore varies from 50 to 226 gallons/hour. A series of tests was run on this embodiment, in which $D_s = 0.75$ inches and $L = 4$ inches to determine the effectiveness of killing several representative species of bacteria. The electrical input to the generator was held at 100 watts, except where indicated for the "control" tests, which is known to produce approximately 75 watts of ultrasonic power from the transducer.

The results of these tests are given below in Tables I-III.

TABLE I

| | Bacteria: E. Coli | | Test No. 1115-1 | |
| --- | --- | --- | --- | --- |
| Series No. | Flow Rate GPH | Bacterial Count* (24 Hr. Growth) | Percent Kill | Ultrasonic Input Power (Watts) |
| 0 - 1 | None | 4.9 × 10⁷ | 0 | None |
| 0 - 2 | 220 | 5.1 × 10⁷ | 0 | None |
| 1 | 220 | 41,800 | 99.2% | 100 |
| 2 | 120 | 26,000 | 99.5% | 100 |

TABLE I-continued

| | | | Test No. 1115-1 | |
|---|---|---|---|---|
| | Bacteria: E. Coli | | | Ultrasonic |
| Series No. | Flow Rate GPH | Bacterial Count* (24 Hr. Growth) | Percent Kill | Input Power (Watts) |
| 3 | 50 | 24,000 | 99.5% | 100 |

*Bacterial Counts represent an average of three (3) replicates.

TABLE II

| | | | Test No. 12175 | |
|---|---|---|---|---|
| | Bacteria: E. Coli | | | Ultrasonic |
| Series No. | Flow Rate GPH | Bacterial Count* (24 Hr. Growth) | Percent Kill | Input Power (Watts) |
| 0 - 1 | None | $1.615 \times 10^8$ | 0 | None |
| 0 - 2 | 202 | $1,613 \times 10^8$ | 0 | None |
| 1 | 202 | 143,000 | 99.11% | 100 |
| 2 | 177 | 71,300 | 99.56% | 100 |
| 3 | 115 | 67,200 | 99.58% | 100 |
| 4 | 54 | 67,000 | 99.58% | 100 |

*Bacterial counts based on 20 replicates.

TABLE III

| | | | Test No. 01066 | |
|---|---|---|---|---|
| | Bacteria S. Aureus | | | Ultrasonic |
| Series No. | Flow Rate GPH | Bacterial Count* (24 Hr. Growth) | Percent Kill | Input Power (Watts) |
| 0 - 1 | None | $1.86 \times 10^7$ | 0 | None |
| 0 - 2 | 226 | $1.85 \times 10^7$ | 0 | None |
| 1 | 226 | 144,000 | 99.22 | 100 |
| 2 | 190 | 59,200 | 99.68 | 100 |
| 3 | 151 | 88,800 | 99.52 | 100 |
| 4 | 85.8 | 92,000 | 99.50 | 100 |
| Bacteria: Salmonella Cholerae-suis | | | | |
| 0 - 1 | None | $2.82 \times 10^7$ | 0 | None |
| 0 - 2 | 226 | $2.78 \times 10^7$ | 0 | None |
| 1 | 226 | 6,000,000 | 79.00 | 100 |
| 2 | 190 | 780,000 | 97.22 | 100 |
| 3 | 151 | 736,000 | 97.38 | 100 |
| 4 | 85.8 | 1,520,000 | 94.58 | 100 |
| Bacteria: Klebsiella Pneumoniae | | | | |
| 0 - 1 | None | $1.95 \times 10^7$ | 0 | None |
| 0 - 2 | 226 | $1.96 \times 10^7$ | 0 | None |
| 1 | 226 | 70,000 | 99.42 | 100 |
| 2 | 190 | 65,000 | 99.66 | 100 |
| 3 | 151 | 60,000 | 99.69 | 100 |
| 4 | 85.8 | 72,000 | 99.63 | 100 |

*Bacterial Counts based on 100 replicates.

The tables show in every case that the use of the ultrasonic energy resulted in a high percentage kill of the bacteria over the range of liquid flow rates employed, but the percentage generally increased at the lower flow rates. From this data, for the bacteria tested, it appears that the optimum flow rate (i.e. the largest flow rate for a high percentage kill) is approximately 150 gallons per hour which is equivalent to 0.158 liters per second. Taking the ultrasonic energy transmitted to the liquid as 75 watts the energy per unit volume of liquid is calculated to be 475 joules/liter for this condition of operation. The criterion for designing a system in accordance with the invention is therefore that the size and power of the transducer must be related to the rate of liquid flow such that the energy per unit volume of liquid must be greater than 475 joules/liter to achieve the degree of kill stated for the particular bacteria. More generally, the system must produce at least 400 joules/liter of ultrasonic energy to be considered an effective disinfectant.

It should be noted that in some circumstances it is not necessary or desirable to achieve the virtual 100% kill demonstrated by the aforesaid tests. The data given here indicate that a reduced kill can be obtained by increasing the rate of liquid flow above the optimum. The system disclosed here is clearly capable of being adjusted to obtain any desired result.

With regard to the mechanical operation of the system, it is important to note that the liquid pressures employed (not exceeding about 40 psi) are sufficiently low that they present no special problem with the pumping equipment. The power output of the ultrasonic transducer is controlled by means of the wave generator so as not to exceed about 25 watts per square centimeter of the active surface in contact with the liquid, which avoids overheating problems with the transducer. The ultrasonic frequency employed may range from about 15–40 kHz but is preferably in the range 20–25 kHz which is a moderate value minimizing mechanical loadings and stress in the transducer. As a result of these designed operating parameters the system is capable of operating continuously for long periods (several months) without maintenance.

An alternative method of describing the manner in which the ultrasonic energy is controlled so as to produce a desired result is to consider the liquid as being exposed to the ultrasonic waves for a period of time which is determined by the rate of liquid flow. It has been found that the action of the ultrasonic waves in a liquid is made evident by the formation of bubbles, due to cavitation, and that these bubbles can be seen to occur for a depth of one or two inches from the active surface of the transducer into the jet. If this distance H is known then the time of exposure of the liquid to ultrasonic energy is given by the equation.

$$T = H/V$$

Where
$T$ = time
$H$ = distance traveled by liquid exposed to ultrasonic energy
$V$ = velocity of liquid For example, in the case discussed previously where the flow rate was 150 gallons/hour, $V$ = 55 feet/second and $H$ = 2 inches which give $T$ = 3 milliseconds (0.003 seconds).

During the period of 3 milliseconds, if the ultrasonic wave frequency is 23.5 kHz the liquid will be subjected to $0.003 \times 23{,}500 = 70$ waves or cycles, each separate wave being responsible for violent local changes of liquid velocity and pressure. It is evident, therefore, that if the liquid rate of flow is increased the number of cycles of wave energy involved will decrease, and the significance of the laboratory test results given in tables I–III can be interpreted as determining the minimum number of cycles required to achieve destruction of the particular bacteria.

To recapitulate, therefore, the invention affords control over all the following variables which are concerned with achieving the desired percentage kill of bacteria:

(a) The concentration of ultrasonic energy per unit volume of liquid;

(b) The time of exposure of the liquid to ultrasonic waves; and (c) The number of ultrasonic waves (cycles) to which the liquid is subjected during its exposure.

The embodiments of the invention in which an exclusive property or privilege is claimed are defined as follows:

1. The method of disinfecting a liquid comprising the steps of continuously discharging a bacteria-containing liquid through a nozzle into the open atmosphere to produce a solid jet of such liquid; directing the liquid jet against an ultrasonically vibrating surface which transversely intercepts the entire cross-section of said jet to impart ultrasonic wave energy lengthwise into said jet; the velocity and cross-section area of said jet and the wave energy emanating from said surface being of such values that at least 400 joules/liter is imparted to the treated liquid.

2. The method of claim 1 wherein said nozzle and surface are spaced apart a distance exceeding the length of visible bubbling agitation of said jet from said surface toward said nozzle.

3. The method of claim 1 wherein said nozzle is oriented to direct the liquid jet vertically upward against said surface for gravity discharge therefrom of an umbrella-shaped sheet of disinfected liquid.

4. The method of claim 1 wherein the power output at said surface is no greater than about 25 watts/cm$^2$.

5. The method of claim 3 wherein said nozzle and surface are spaced apart a distance several times the diameter of the nozzle orifice to provide a jet of progressively increasing cross-section diameter upwardly from said nozzle; and wherein said surface is of diameter approximately equal to the cross-section diameter of said liquid jet where intercepted by said surface.

* * * * *